United States Patent [19]
Chiu et al.

[11] Patent Number: 5,553,607
[45] Date of Patent: Sep. 10, 1996

[54] PORTABLE STEAM INHALATOR

[75] Inventors: Bernard Chiu, Wellesley; Randolph E. Maxwell, Upton, both of Mass.; Stephen M. Gatchell, Warwick; Jerald Bradley, East Providence, both of R.I.; John Longan, Natick; Rodney Jané, Westboro, both of Mass.

[73] Assignee: Duracraft Corporation, Southborough, Mass.

[21] Appl. No.: 425,010

[22] Filed: Apr. 17, 1995

[51] Int. Cl.⁶ .................................................. A61M 16/10
[52] U.S. Cl. ................................ 128/203.26; 128/209.13
[58] Field of Search .......................... 128/203.12, 203.26, 128/204.13, 204.14

[56] References Cited

U.S. PATENT DOCUMENTS 4,019,511  4/1977  Choporis et al. ..................... 128/212
4,319,566  3/1982  Hayward et al. ..................... 128/203.26

*Primary Examiner*—Edgar S. Burr
*Assistant Examiner*—Eric P. Raciti
*Attorney, Agent, or Firm*—John E. Toupal; Harold G. Jarcho

[57] ABSTRACT

A portable inhalator including a housing defining an inhalation chamber with a discharge opening for accommodating a breath supporting body portion, an exhaust passage terminating with an exhaust opening and isolated from the inhalation chamber, and a liquid reservoir communicating therewith. Also included are a burner for heating liquid in the reservoir, a fuel canister removably supported by the housing, and a valve for controlling fuel flow between the canister and the burner.

7 Claims, 2 Drawing Sheets

PORTABLE STEAM INHALATOR

BACKGROUND OF THE INVENTION

This invention relates generally to a portable steam inhalator and, more particularly, to a portable steam inhalator which does not require electrical operating power.

Portable steam inhalators are used for various types of respiratory therapy. Prior portable steam inhalators typically employ electrical heating elements to generate steam by boiling water in a liquid reservoir. The resultant steam is directed to a mask shaped to accommodate the nose and mouth of a person receiving therapy. Such prior inhalators provide effective therapy in those situations in which electrical power is available and convenient support accommodations exist for patient and inhalator. However, respiratory therapy often is desired or required in remote environments in which electrical power and suitable support accommodations are not available.

The object of this invention, therefore, is to provide an improved, portable steam inhalator that can be used to provide respiratory therapy in remote locations wherein electrical power and convenient support fixtures are unavailable.

SUMMARY OF THE INVENTION

The invention is a portable inhalator including a housing defining an inhalation chamber with a discharge opening for accommodating a breath supporting body portion, an exhaust passage terminating with an exhaust opening and isolated from the inhalation chamber, and a liquid reservoir communicating therewith. Also included are a burner for heating liquid in the reservoir, a fuel canister removably supported by the housing, and a valve for controlling fuel flow between the canister and the burner. Isolation of the inhalation chamber insures against inhalation of exhaust fumes.

According to features of the invention, the discharge opening is disposed between the reservoir and the exhaust opening, and the housing further defines an inlet opening for introducing ambient air into the inhalation chamber and disposed between the reservoir and the exhaust opening. These features facilitate the addition of fresh air to steam produced in the reservoir and prevent undesirable flow of exhaust fumes into the inhalation chamber.

According to another feature of the invention, the inhalator includes a liquid absorbent material disposed in the reservoir. By absorbing liquid in the reservoir, the absorbent material enhances operating efficiency.

According to other features of the invention, the inhalator includes a tank having a supply spout terminating adjacent to a bottom of the reservoir so as to provide a controlled discharge of liquid into the reservoir and maintain a predetermined maximum water level therein. This feature also improves operating efficiency.

According to still other features of the invention, the housing is removably secured to an upper end of the canister, and further defines a burner cavity retaining the burner, communicating with the exhaust passage, and hermetically isolated from the inhalation chamber; the reservoir is disposed between the burner cavity and the discharge opening; and the exhaust opening is spaced from the discharge opening in a direction away from the burner cavity. This placement of the exhaust opening prevents exhaust fumes exiting the exhaust opening from rising into a region accessible to breathing body portions of a user.

According to one embodiment of the invention, the housing includes a heat exchanger tube defining the reservoir and extending between the burner cavity and the inhalation chamber; the tube is substantially filled with absorbent material and has at one end an outlet port disposed in the inhalation chamber, and at an opposite end an inlet port communicating with the supply opening of the tank. The absorbent material filled exchanger tube enhances operating efficiency.

DESCRIPTION OF THE DRAWINGS

These and other objects and features of the invention will become more apparent upon a perusal of the following description taken in conjunction with the accompanying drawings wherein.

DESCRIPTION OF THE PREFERRED EMBODIMENTS

Figure 1:
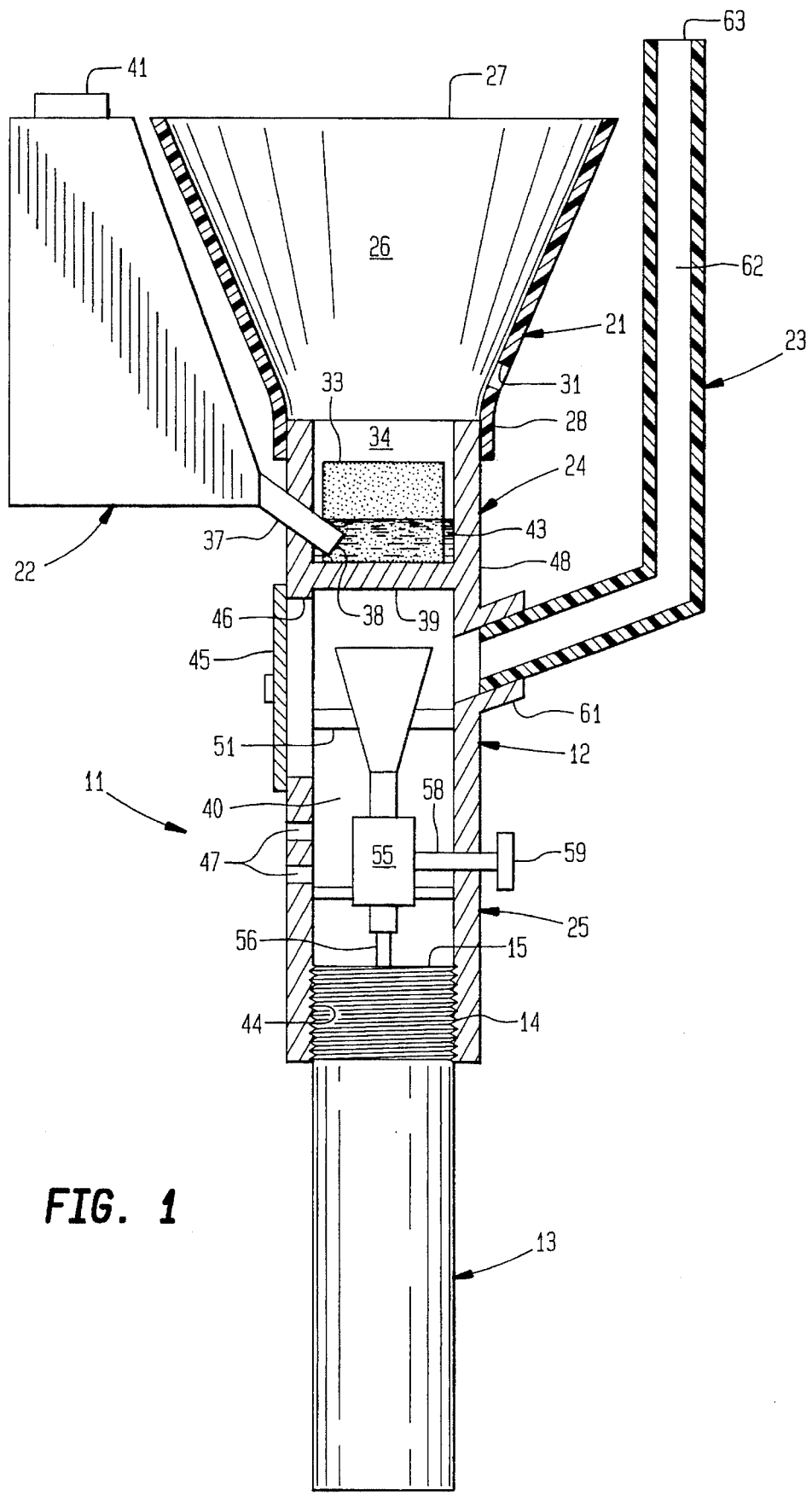
FIG. 1 is an elevational cross-sectional view of a portable steam inhalator.

A portable steam inhalator 11 includes a housing 12 removably secured to a cylindrical canister 13 preferably filled with butane fuel. Receiving the housing 12 are external threads 14 on an upper end 15 of the fuel canister 13. The bottom portion of this canister 13 serves as a handle for the inhalator 11.

Forming the housing 12 are a conically shaped inhalation mask portion 21, a tank housing portion 22, an exhaust tube housing portion 23, a reservoir housing portion 24 and a burner housing portion 25. The inhalation portion 21 encloses an inhalation chamber 26 and has an upwardly directed larger open end defining a discharge opening 27 and a downwardly directed smaller end 28 communicating with an open upper end of the reservoir portion 24. A pad made of a suitable liquid absorbent material 33 is retained at the bottom of a reservoir 34 formed by the dish-shaped reservoir housing portion 24.

The liquid supply tank 22 includes at its lower end a liquid supply tube 37 that extends into the reservoir 34. Defined at the lower end of the supply tube 37 is a liquid supply opening 38 positioned directly adjacent to a bottom wall 39 of the reservoir portion 24. An air tight cap 41 is received by an opening at the top of the supply tank 22. Liquid within the tank 22 discharges through the supply tube 38 to maintain a given maximum level of liquid 43 in the reservoir 34. That maximum liquid level is maintained in a well known manner at approximately the level of the supply opening 38 by the differential pressures existing within the sealed tank 22 and in the inhalation chamber 26. Most of the water retained in the reservoir 34 is absorbed by the absorbent pad 33.

The burner housing portion 25 is a hollow cylinder with an upper end joined to the bottom wall 39 and a lower end having internal threads 44 which engage the threads 14 on the fuel canister 13. A door 45 covers an opening 46 that provides access to a burner cavity 40 defined by the burner portion 25. Also formed in the cylindrical burner portion 25 are burner intake openings 47.

A bracket 51 within the burner cavity 41 supports a burner 52 disposed adjacent to the bottom wall 39 of the reservoir portion 24. Connected to the burner 52 is a control valve 55 removably coupled to a hollow stem 56 extending out of the fuel canister 13. A shaft 58 extending through the cylindrical burner portion 25 has an inner end coupled to the control valve 55 and an outer end connected to an actuator knob 59. Preferably, the burner housing portion 25 and the reservoir housing portion 24 are an integrally formed unit that carries the tank 22, the flexible inhalation mask 27 and the exhaust tube 23.

A lower end of the exhaust tube 23 is press-fitted into a hollow cylindrical appendage 61 formed at an upper end of the burner portion 25. Formed by the tube 23 is an exhaust passage 62 terminating at an outer end with an exhaust opening 63 positioned above the inhalation mask 21. Thus, both the discharge opening 27 and the inlet opening 28 of the inhalation chamber 26 are disposed between the reservoir 34 and the exhaust opening 63 of the exhaust tube 23.

During use of the inhalator 11, the fuel canister 13 conveniently functions as a handle for a person desiring respiratory therapy. After opening of the control valve 55 with the actuator knob 59, the door 45 is opened to provide access to the cavity 40 and facilitate ignition of the burner 52. A resultant flame provides heat that is transferred by the bottom wall 39 to the liquid 43 in the reservoir 34 producing within the chamber 26 steam that is discharged through the discharge opening 27. Mixed with the steam is a supply of air passing through the intake opening 31 in the inhalation mask 21. The combined air and steam is received by breath supporting body portions (mouth and/or nose) of a user desiring respiratory therapy. Exhaust fumes generated in the burner cavity 40 pass through the exhaust tube 23 and out of the exhaust opening 63 at a location above the nose and mouth of the user thereby preventing the undesirable inhalation of combustion products.

Figure 2:
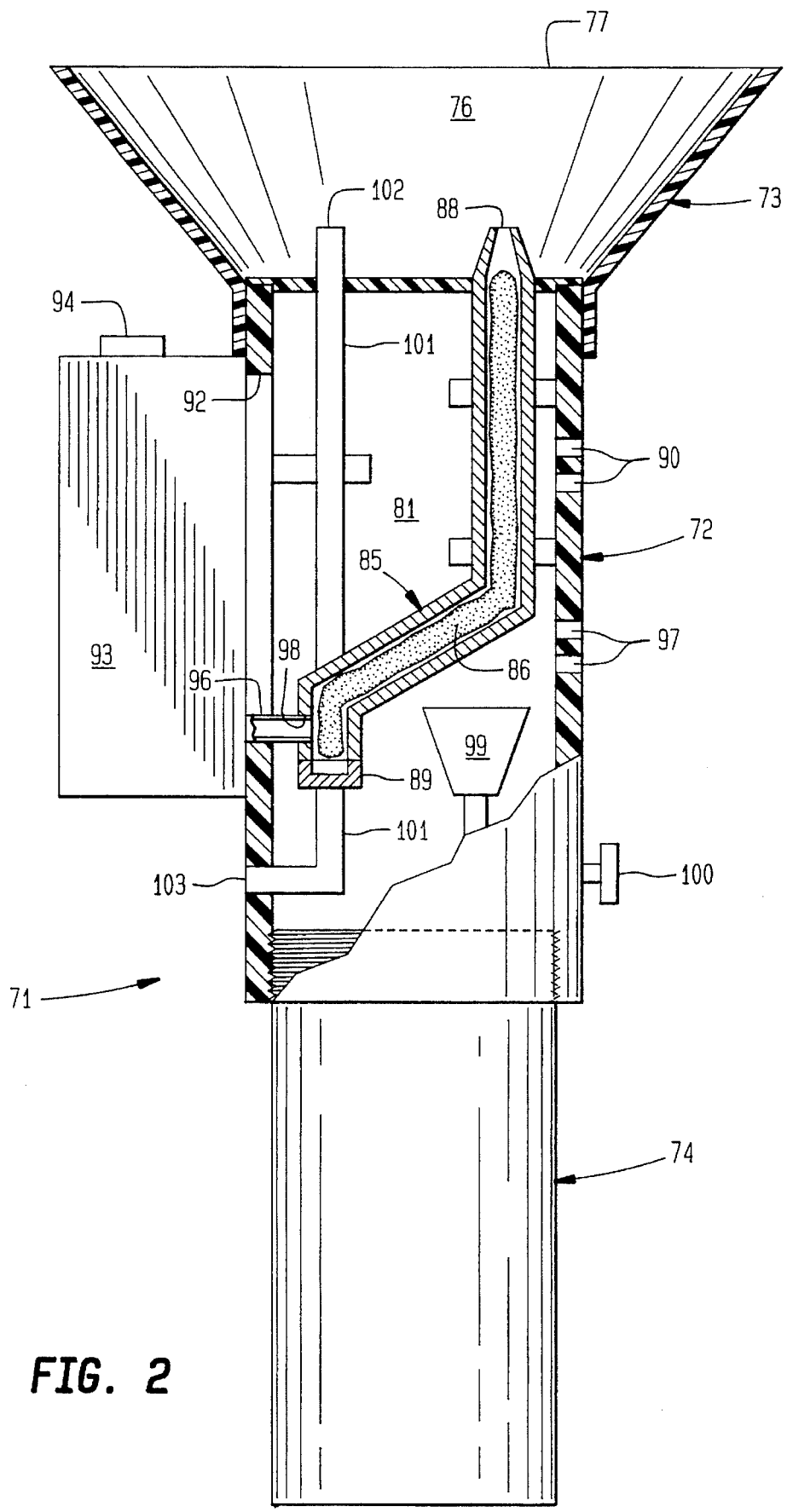
FIG. 2 is an elevational cross-sectional view of a second portable steam inhalator embodiment.

Illustrated in FIG. 2 is another inhalator embodiment 71 of the invention. The inhalator 71 includes a hollow cylindrical burner portion 72 straddled by a conically shaped inhalation mask portion 73 and a butane canister 74. Formed by the inhalation mask 73 is an inhalation chamber 76 having an upwardly directed discharge opening 77. The burner portion 72 defines a burner cavity 81 isolated from the inhalation chamber 76 by a sealing membrane 82.

Retained within the burner cavity 81 is a heat exchanger reservoir tube 85 substantially filled with a liquid absorbing material 86. An upper end of the tube 85 projects through the sealing membrane 81 and defines an outlet nozzle 88 disposed within the inhalation chamber 76. Closing a lower end of the tube 85 is a cap 89. Exhaust openings 90 communicate with the burner cavity 81. Covering an opening 92 in the burner portion 72 is a detachable, arcuately shaped liquid tank 93. A fluid tight cap 94 can be removed to allow filling of the tank 63 with a liquid such as water. Formed at a lower end of the tank 93 is a supply spout 96 that is press fitted into a receiving cylindrical opening 98 at the lower end of the heat exchanger tube 85.

A burner 99 is mounted within the burner cavity 81 and receives air through intake openings 97 in the burner portion 72. The burner 99 communicates with the fuel canister 74 via a control valve (not shown) operated by a knob 100. Extending through the burner cavity 81 and the sealing membrane 82 is an air supply tube 101. An upper end of the tube 101 defines an air supply orifice 102 positioned within the inhalation chamber 76 while a lower end defines an intake orifice 103 located below the level of the burner 99.

During use of the inhalator 71, the supply tank 93 maintains a given maximum liquid level in the heat exchanger tube 85 in the manner described above for the inhalator embodiment 11. Water absorbed by the absorbent material 86 is heated by flame emanating from the burner 99 via the conductive walls of the tube 85. Resultant steam is discharged by the outlet nozzle 88 into the inhalation chamber 76 and mixed with ambient air supplied by the air supply tube 101. The combined air and steam within the chamber 76 is available at the discharge opening 77 to the breathing body portions of a person desiring respiratory therapy. Because of the location of the air intake orifice 103 below the burner 99, the air supplied by the air supply tube 101 is free of combustion products generated in the burner cavity 81.

Obviously, many modifications and variations of the present invention are possible in light of the above teachings. It is to be understood, therefore, that the invention can be practiced otherwise than as specifically described.

What is claimed is:

1. A portable inhalator comprising:

a housing defining an inhalation chamber with a discharge opening adapted to receive a breath supporting body portion, an exhaust passage terminating with an exhaust opening and isolated from said inhalation chamber, a reservoir for retaining a liquid and communicating with said inhalation chamber, and a burner cavity communicating with said exhaust passage and hermetically isolated from said inhalation chamber;

a burner retained in said burner cavity and disposed to heat liquid in said reservoir;

a fuel canister removably supported by said housing means;

a valve for controlling fuel flow between said canister and said burner and a tank for retaining liquid and having liquid supply opening communicating with said reservoir; and wherein said housing comprises a heat exchanger tube defining said reservoir and extending between said burner cavity and said inhalation chamber; said tube being substantially filled with absorbent material, having one end disposed in said inhalation chamber and defining an outlet port, and an opposite end defining an inlet port communicating with said supply opening.

2. An inhalator according to claim 1 wherein said discharge opening is disposed between said reservoir and said exhaust opening.

3. An inhalator according to claim 2 wherein said housing further defines an inlet opening for introducing ambient air into said inhalation chamber and disposed between said reservoir and said exhaust opening.

4. An inhalator according to claim 1 wherein said tank comprises a supply spout terminating with said supply opening, and said supply opening is disposed adjacent to a bottom of said reservoir.

5. An inhalator according to claim 1 wherein said reservoir is disposed between said burner cavity and said discharge opening, and said exhaust opening is spaced from said discharge opening in a direction away from said burner cavity.

6. An inhalator according to claim 1 including an air supply tube with an intake orifice located below said burner and an air supply orifice located in said inhalation chamber.

7. An inhalator according to claim 6 wherein said air supply tube extends through said burner cavity.

* * * * *